US010091574B2

(12) United States Patent
Smith et al.

(10) Patent No.: US 10,091,574 B2
(45) Date of Patent: Oct. 2, 2018

(54) METHOD AND APPARATUS FOR DELIVERING AUDIO SIGNALS AND PROVIDING HEARING PROTECTION DURING MEDICAL IMAGING

(71) Applicant: Neocoil, LLC, Pewaukee, WI (US)

(72) Inventors: Terry Smith, Waukesha, WI (US); Paul Ropella, New Berlin, WI (US); Matthew Brown, Mukwonago, WI (US); Cindy Comeau, Brookfield, WI (US); Brian Brown, Wauwatosa, WI (US)

(73) Assignee: Neocoil, LLC, Pewaukee, WI (US)

( * ) Notice: Subject to any disclaimer, the term of this patent is extended or adjusted under 35 U.S.C. 154(b) by 88 days.

(21) Appl. No.: 14/952,575

(22) Filed: Nov. 25, 2015

(65) Prior Publication Data

US 2017/0150247 A1 May 25, 2017

(51) Int. Cl.

| | |
|---|---|
| ***A61F 2/20*** | (2006.01) |
| ***H04R 1/10*** | (2006.01) |
| ***H04R 1/02*** | (2006.01) |
| ***H04R 1/28*** | (2006.01) |
| ***H04R 1/34*** | (2006.01) |

(52) U.S. Cl.
CPC ............. *H04R 1/1083* (2013.01); *H04R 1/02* (2013.01); *H04R 1/2876* (2013.01); *H04R 1/345* (2013.01); *H04R 1/1016* (2013.01)

(58) Field of Classification Search
CPC ...... H04R 1/1083; H04R 1/02; H04R 1/1016; H04R 1/2876; H04R 1/1091; H04R 1/10
USPC ................................................. 381/72; 180/2
See application file for complete search history.

(56) References Cited

U.S. PATENT DOCUMENTS

| | | | | |
|---|---|---|---|---|
| 5,277,184 | A | 1/1994 | Messana | |
| 5,313,945 | A * | 5/1994 | Friedlander ........ | G01R 33/3854 324/318 |
| 5,577,504 | A | 11/1996 | Salloway et al. | |
| 5,987,672 | A * | 11/1999 | Oosterwaal ............ | G01R 33/28 324/318 |
| 7,292,704 | B2 | 11/2007 | Lederer | |
| 7,609,844 | B2 | 10/2009 | Lederer | |
| 8,103,014 | B2 | 1/2012 | Porzelt et al. | |
| 8,170,262 | B1 * | 5/2012 | Liu ...................... | H04R 1/1016 381/382 |

(Continued)

OTHER PUBLICATIONS

Magnacoustics Genesis Ultra; "Communication & Music System for MRI"—(2 pages).

(Continued)

*Primary Examiner* — Vivian Chin
*Assistant Examiner* — Ammar Hamid
(74) *Attorney, Agent, or Firm* — Boyle Fredrickson, SC

(57) ABSTRACT

A pneumatic audio system which is compatible with use within an MRI environment is disclosed. The system has an audio transducer including a housing having a plurality of walls, a foam insert supported within the housing, and a speaker supported by the foam insert and extending at an angle with respect to the walls of the housing. The system further has a hollow tube coupled to the audio transducer at a first end and configured to transmit audio signals from the speaker through the tube. The system further has an earphone coupled to a second end of the hollow tube and configured to deliver audio signals to an ear canal of a human user.

17 Claims, 11 Drawing Sheets

(56) References Cited

U.S. PATENT DOCUMENTS

| | | | | |
|---|---|---|---|---|
| D708,930 | S | 7/2014 | Rothbaum et al. | |
| 2002/0055374 | A1 * | 5/2002 | Rivera | H04B 1/3838 455/569.1 |
| 2006/0072770 | A1 * | 4/2006 | Miyazaki | H04R 19/02 381/116 |
| 2008/0118077 | A1 | 5/2008 | Rasmussen | |
| 2010/0128905 | A1 | 5/2010 | Warrent et al. | |
| 2011/0170730 | A1 | 7/2011 | Zhu | |
| 2014/0105430 | A1 | 4/2014 | Yang | |
| 2015/0305462 | A1 * | 10/2015 | Rothbaum | B65D 63/10 224/575 |

OTHER PUBLICATIONS

Resonance Technology, Inc.; "SereneSound"; "SereneSound's State-of-the-Art Headset and Transducer"—(2 pages).

Optoacoustics, Ltd.; "IMROC Interventional MR Optical Communication System";—(3 pages).

Nordic Neurolab; "AudioSystem High-end audio solution for fMRI";—(2 pages).

International Search Report and the Written Opinion of the International Searching Authority dated Mar. 24, 2017; International Patent Application No. PCT/US2016/063496, International Filing Date Nov. 23, 2016—(12) pages.

* cited by examiner

METHOD AND APPARATUS FOR DELIVERING AUDIO SIGNALS AND PROVIDING HEARING PROTECTION DURING MEDICAL IMAGING

BACKGROUND OF THE INVENTION

The subject matter disclosed herein relates to a pneumatic audio system for use in magnetic field environments. More specifically, a system for wirelessly transmitting audio signals from a remote device to a transducer module connectable to hollow tubing and communicating the audio signals via the hollow tubing to a headphone during imaging.

As is known to those skilled in the art, a magnetic resonance imaging (MRI) system uses a magnetic field and pulses of radio wave energy to produce pictures of internal organs of the body. The magnetic field is created by running an electrical current through a coiled wire—an electromagnet. When the current is switched on, an outward force is produced along the coil in a short amount of time. This causes the coil to expand and vibrate, resulting in loud clicking noise. The current is switched on and off rapidly, producing a loud sound that is amplified by the enclosed space and vibrations of the equipment.

The loud sounds of an MRI scanner cause many disturbances to the patients receiving the scan and the healthcare professional administering the scan. The noises of the MRI scanner may cause annoyance, verbal communication difficulties, hearing loss, and anxiety to the patient, sometimes causing them to fidget which results in distorted imaging. Providing the patient with headphones having cups configured to encompass the ear canal can reduce the level of noise in the MR environment. However, traditional hearing protection headphones further reduce the ability of a healthcare professional to communicate with the patient.

Thus, it has been known to provide headphones in which a speaker is provided in the earcup. Electronic signals including audio data spoken by the healthcare professional may be provided to the speaker for reproduction and transmission to the patient. Providing the speaker within the earcup thereby provides both a level of hearing protection from ambient noise and allows communication from the healthcare professional to be delivered to the patient. However, the earcups themselves are bulky and may not be suited for use within an antenna array configured to image a patient's head. Additionally, the components used for audio transmission, as well as the for hearing protection may result either in interference with the magnetic field of the MRI scanning or additional artifacts appearing on the image. Thus, it would be desirable to provide an improved headset for use during head imaging that provides both sound protection for the patient and allows for communication with the healthcare professional.

BRIEF DESCRIPTION OF THE INVENTION

The present invention provides headphones that are compatible with an MRI environment which isolate external sounds from the MRI and funnel desired sound through the headphone.

The subject matter disclosed herein describes a pneumatic audio system which is compatible with use within an MRI environment. According to one embodiment of the invention, sound system for use in a magnetic field environment is provided. The system has an audio transducer including a housing having a plurality of walls, a sound insulating insert supported within the housing, and a speaker supported by the sound insulating insert and extending at an angle with respect to the walls of the housing. The system further has a hollow tube coupled to the audio transducer at a first end and configured to transmit audio signals from the speaker through the tube. The system further has a headphone coupled to a second end of the hollow tube and configured to deliver audio signals to an ear canal of a human user.

It is an objective of the present invention to provide an audio transducer that minimizes the vibrations of an MRI scanner by insulating the speaker from sounds outside the housing of the transducer.

The housing may include a port receiving an end of the hollow tube and releasably mounted to the housing. The port may be released, for example, when a button of the housing is pressed.

It is an objective of the present invention to provide a quick disconnect of the hollow tubing to the audio transducer.

The speaker may be angled with respect to the housing walls.

It is an objective of the present invention to direct the sound toward the center of the transducer for better transmission of sound.

The housing may include an outwardly extending bracket permitting the hollow tube to be wrapped around the bracket for storage.

It is an objective of the present invention to allow the tubing to be wound around the audio transducer for easy storage.

The speaker may be a piezoelectric speaker.

It is an objective of the present invention to provide a small and compact sound producer.

The speaker may be spaced from the walls of the housing by the sound insulating insert.

It is an objective of the present invention to prevent vibrating sound from entering the audio transducer by isolating the speaker from the housing walls.

The audio transducer may also include an RF receiver operable to wirelessly receive an audio signal, and a processor operable in communication with the RF receiver and the speaker, wherein the processor transmits the audio signal to the speaker.

It is an objective of the present invention to allow a medical professional to communicate with the patient from another room or other remote source.

According to another embodiment of the invention, a pneumatic audio system for use during magnetic resonance (MR) imaging is disclosed. The system includes an audio transducer, a first hollow tube having a first end and a second end wherein the audio transducer is connected at the first end of the first hollow tube, a second hollow tube having a first end and a second end wherein the first end of the second hollow tube is connectable to the second end of the first hollow tube, and an earphone wherein the second end of the second hollow tube is connectable to the earphone. The first hollow tube generates an artifact within an MR image responsive to the magnetic field generated by an MR scanner and the second hollow tube does not generate an artifact within an MR image responsive to the magnetic field.

It is an objective of the present invention to provide an all plastic construction that makes the tubing inert and invisible to the MRI scan.

It is an objective of the present invention to isolate the invisible tubing to those areas being scanned as a way to reduce costs.

According to other aspects of the invention, the system may have a fitting coupling the first hollow tube to the second hollow tube. A housing may be included to receive the fitting. A clip may be provided on the housing for attachment to a patient or to a patient's clothing.

According to another embodiment of the invention an earphone for transmitting and receiving audio signals is disclosed. The earphone includes a hollow tubing configured to transmit audio signals therethrough, a housing providing a channel for receiving the flexible tubing therein and bending at a substantially perpendicular angle while terminating at a nozzle guide sized to receive the hollow tubing therein, and a plug for insertion into an ear canal having a passage sized therein for receiving the nozzle guide. The hollow tubing is received in the channel and extends through the nozzle guide to terminate at the distal end of the ear canal plug.

It is an objective of the present invention to provide an ear canal plug that directs sound into the inner ear.

According to other aspects of the invention, the headphone includes a second housing portion coupled to the housing and fastening the tubing in place. The ear canal plug may be a foam plug, and the nozzle guide may have a length less than a length of the ear canal plug.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Various exemplary embodiments of the subject matter disclosed herein are illustrated in the accompanying drawings in which like reference numerals represent like parts throughout, and in which.

Figure 1:
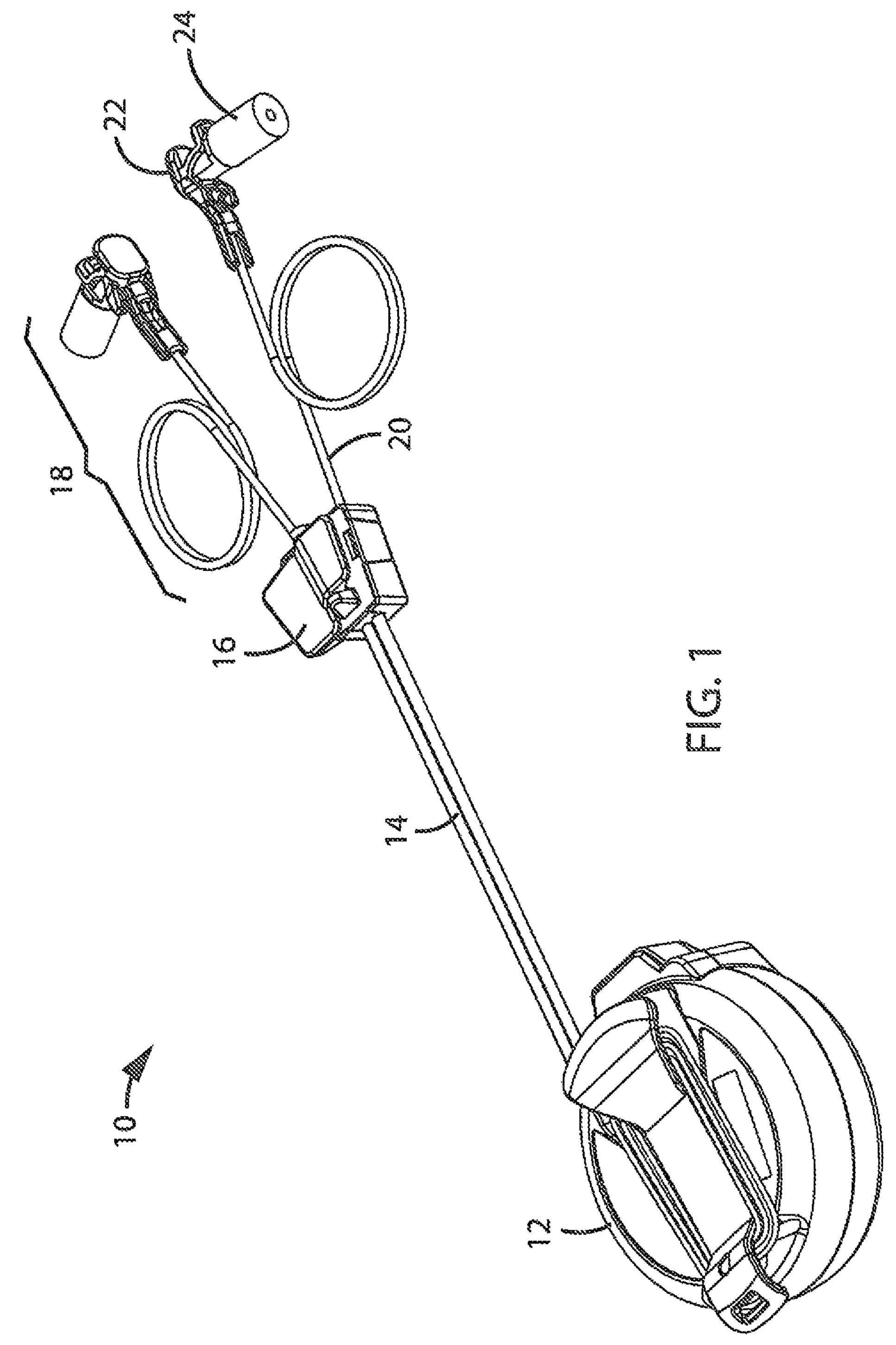
FIG. 1 is an isometric view of an audio assembly according to one embodiment of the present invention providing a transducer module, pneumatic tubing, and headphones.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements and/or wireless connection where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

According to one embodiment of the present invention, a pneumatic audio system, providing an audio transducer, pneumatic tubing, and headphones, for use with patients in a magnetic field environment, is disclosed. The pneumatic audio system may be used in a MRI environment. Alternatively, the present invention may be implemented in a CT other imaging environment as understood in the art. While the noise levels in a CT environment are generally not as loud as in a MRI environment, the problems of keeping the patient calm and maintaining verbal communication exist in both environments. The present invention allows the pneumatic audio system to be used in any healthcare environment, regardless of the scanner being used or the medical test being administered.

Referring to FIG. 1, one embodiment of the pneumatic audio system 10 is shown. The pneumatic audio system 10 is compatible with a MRI environment such that it does not interfere with the magnetic field environment or the imaging of the MRI scanner. The pneumatic audio system 10 provides an audio transducer 12, pneumatic or hollow tubing 14, a splitter 16, and a headphone assembly 18. According to the illustrated embodiment, the headphone assembly 18 includes two earphones 17, one for each ear. It is contemplated, that the headphone assembly 18 may include a single earphone 17 for use in one ear of the patient and a conventional ear plug, without a passageway extending through it, for use in the other ear of the patient. The headphone assembly 18 provides MR "invisible" tubing 20, a tubing retainer 22, and ear canal plugs 24. As will be discussed in more detail below, the MR "invisible" tubing 20 is a hollow tubing made of a material that is not excited by the magnetic pulses from the MR scanner, such that the antenna arrays do not detect a responsive signal from the MR invisible tubing 20. Because the material of the MR invisible tubing 20 does not generate a signal responsive to the magnetic pulses from the MR scanner, it does not appear in the MR image resulting from the MR scan.

Figure 2:
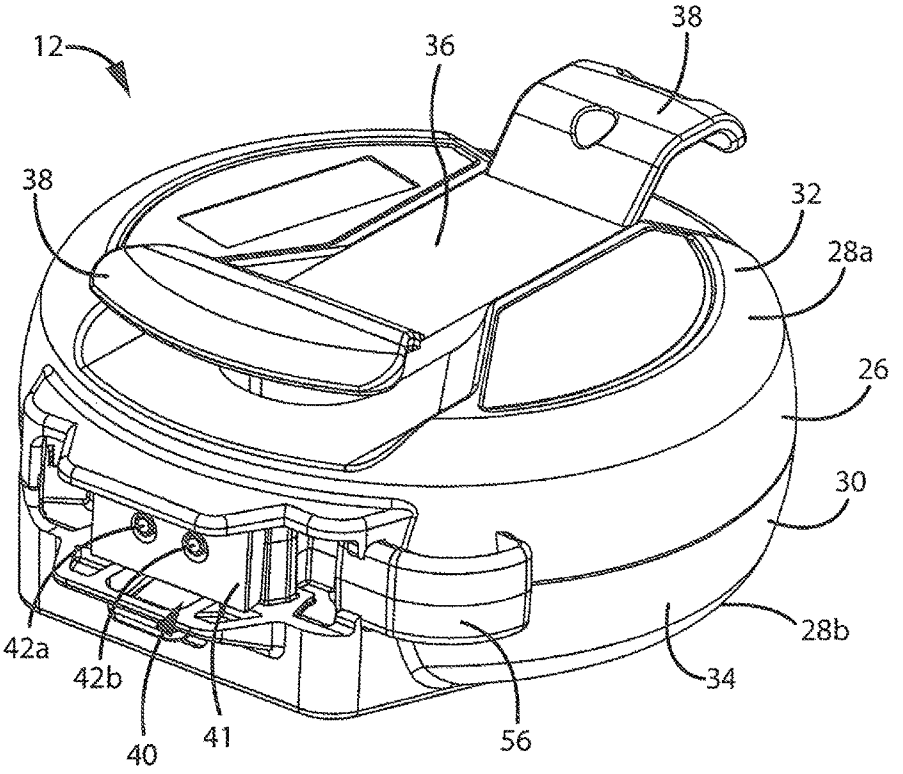
FIG. 2 is an isometric view of the transducer module of FIG. 1 showing a cylindrical housing with a tubing wraparound bracket.
Figure 3:
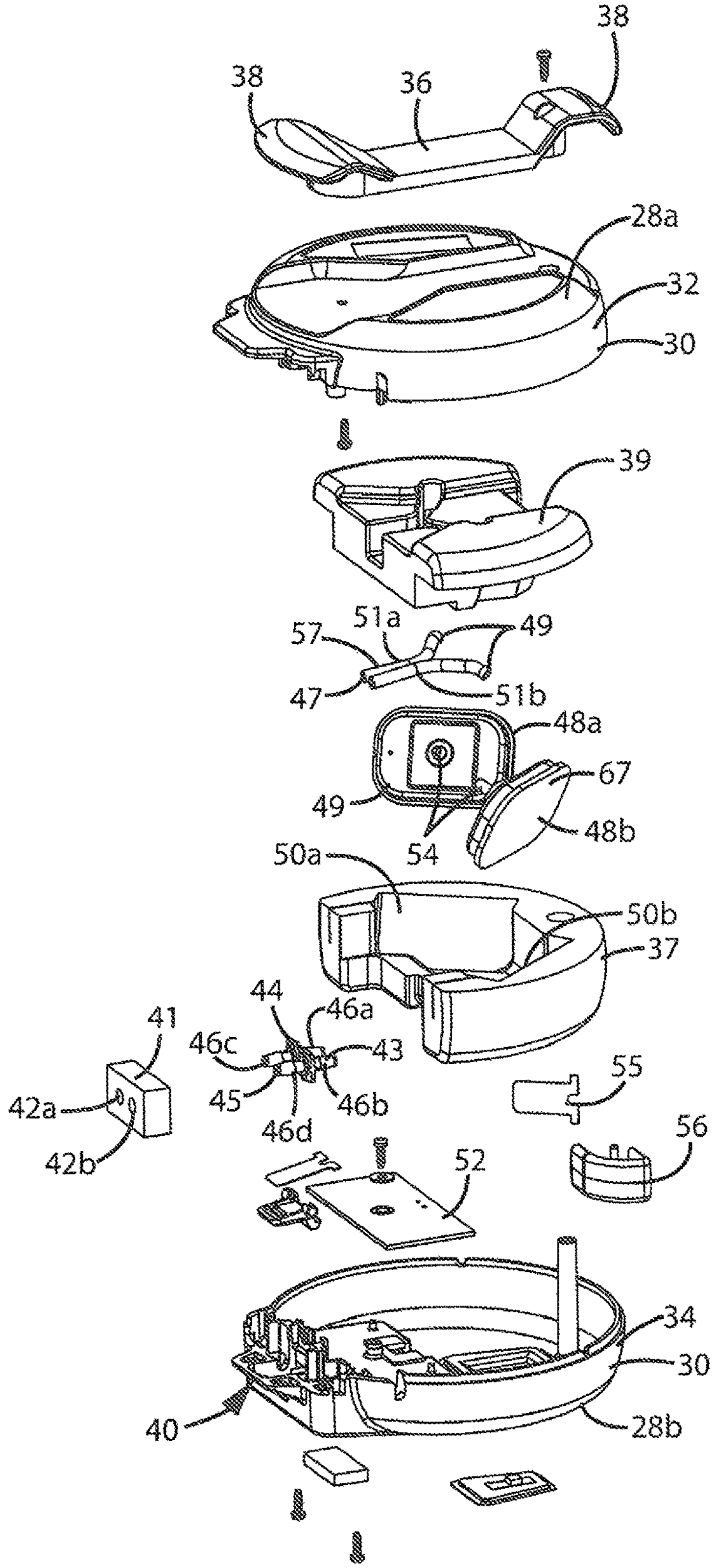
FIG. 3 is a partially exploded view of the transducer module of FIG. 1.

Referring to FIGS. 2 and 3, the audio transducer 12 is defined by a generally cylindrical housing 26, having two parallel bases 28*a*, 28*b* connected by a curved surface 30. The cylindrical housing 26 is separable into a top half 32 and bottom half 34 dividing the cylindrical housing 26 longitudinally along the curved surface 30.

An opening 40 is provided along the curved surface 30 of the housing 26 for permitting audio communication between the hollow tubing 14 and structures within an interior of the housing 26. The opening 40 is generally rectangular shaped and sized to receive a cuboid foam hose connector 41. The foam connector 41 has two spaced passages 42*a*, 42*b* therein such that when the foam connector 41 is received within the opening 40, the passages 42*a*, 42*b* extend between an exterior of the housing 26 and an interior of the housing 26. The passages 42*a*, 42*b* are generally circular in shape and correspond in size to receive a first end of a dual tube, two sided fitting 44.

The dual tube, two sided fitting 44 provides passages to joining two tubes to be connected on a first end 43 with two tubes of a same or different size to be connected on a second end 45. Each end 43, 45 includes a pair of couplings to which tubes may be connected. A first coupling 46*a* of the first end 43 may communicate with a first coupling 46*c* of the second end 45, and a second coupling 46*b* of the first end may communicate with a second coupling 46*d* of the second end 45. As shown, the second end 45 of the dual tube, two sided fitting 44 is inserted within the passages 42*a*, 42*b* of the foam connector, and the first end 43 of the dual tube, two sided fitting 44 is connected to two tubes of a Y-tubing 57. As such, a first tube 46*c* of the second end 45 of the two sided fitting 44 communicates with the first passage 42*a* of the foam connector 41 and a second tube 46*d* of the second end 45 of the two sided fitting 44 communicates with the second passage 42*b* of the foam connector 41. The first passage 46*a* of the first end 43 of the two sided fitting 44 communicates with a first tube 51*a* of the Y-tubing 57 and the second passage 46*b* of the first end 43 of the two sided fitting 44 communicates with a second tube 51*b* of the Y-tubing 57.

The Y-tubing 57 may be formed, for example, from a polyvinyl chloride (PVC) tubing such as that marketed under the name Tygon® R-3400. The Y-tubing 57 provides a first end 47 wherein the first tube 51*a* and the second tube 51*b* of the Y-tubing 57 converge, and a second end 49 wherein the first tube 51*a* and the second tube 51*b* of the Y-tubing 57 diverge. According to the illustrated embodiment, the second end 49 of the Y-tubing 57 diverges at a generally ninety degree angle. The first end 47 of the Y-tubing is connected to the first end 43 of the two sided fitting 44 and the second end 49 is connected to speakers 48*a*, 48*b*.

The interior of the housing 26 provides a bottom foam insert 37 seated within the bottom half 34 of the housing 26. The bottom foam insert 37 is sized to be fitted within the interior of the housing 26 and may be at least half of the size of the bottom half 34 of the housing. The bottom foam insert 37 provides two speaker beds 50*a*, 50*b* along an angled edge of the foam insert 37. The speaker beds 50*a*, 50*b* are rectangular cutouts providing a receiving surface for the speakers 48*a*, 48*b* where the speaker beds 50*a*, 50*b* are angled toward a center of the housing 26. The speaker beds 50*a*, 50*b* are arranged approximately ninety degrees apart. A top foam insert 39 mates with the bottom foam insert 37 and is seated partially within the bottom foam insert 37 to provide a generally solid foam piece with the exception of the hollow space provided around the two speaker beds 50*a*, 50*b* providing a space for the speakers 48*a*, 48*b* to be installed. The top foam insert 39 and bottom foam insert 37 provide insulation between the housing 26 and the speakers 48*a*, 48*b* to insulate the speakers 48*a*, 48*b* from unwanted noise and vibrations translated from the ambient MR environment through the housing 26.

The speakers 48*a*, 48*b* are preferably piezoelectric material housed within a generally thin rectangular housing 67 sized to fit within the speaker beds 50*a*, 50*b*. The speakers 48*a*, 48*b* are installed within the speaker beds 50*a*, 50*b*, respectively, such that the speakers 48*a*, 48*b* rest at an angle resembling the angle of the speaker beds 50, 50*b*. In this respect, a face of the speakers 48*a*, 48*b* are angled toward a center of the housing 26 and are arranged approximately ninety degrees apart. The face of the speakers 48*a*, 48*b* is preferably located at an angle of 40-80 degrees with respect to the base 28*b*.

The face of the speakers 48*a*, 48*b* extending toward the center of the housing 26 provides a conical protrusion having a tubing connector 54 for connection to the Y-tubing 57. In this respect the audible sound produced by the piezoelectric material is translated through the tubing connector 54 to the Y-tubing 57.

The speakers 48*a*, 48*b* are electrically connected to a circuit board 52 located within the housing 26. Each speaker 48 receives a sound signal represented, for example, as a voltage signal. When the voltage signal is delivered to the piezoelectric material, it is converted to an audible sound using the diaphragms and resonators of the speaker, as understood in the art. It is contemplated that the sound signal may be delivered wirelessly from a transmitting device (not shown) located in the MRI environment or in an adjacent control room that is insulated from the magnetic environment. The sound signals may use radio frequency (RF) waves transmitted from the RF transmitting device to a RF receiver device of the audio transducer 12. The receiver (not shown) is mounted on the circuit board 52 and includes a receive circuit operable to receive the transmitted signal from the transmitting device and converts the RF signal to a digital signal suitable, for example, as an input to a processor in communication with the receive circuit. The processor converts the received audio signal to an output signal which may be provided directly or through a driver circuit to the piezoelectric speaker 48 such that the speaker 48 may reproduce the original sound signal.

The housing 26 may further provide a manual actuator for releasing a quick disconnect coupler 58 mounted to the hollow tubing 14. The manual actuator may be a button, lever, slide, or any other suitable actuator. According to the illustrated embodiment, the manual actuator is a button 56 located near the opening 40 where the quick disconnect coupler 58 is attached. The button 56 may be attached to a spring 55 and biased toward a lock position that retains the quick disconnect coupler 58 to the housing. Pressing the button 56 compresses the spring and moves the button 56 toward an unlock position away from the coupler 58, releasing the coupler 58 from its connection to the housing 26.

An outer surface of the top half 32 of the housing 26 may include a bracket 36 serving as a tubing retaining structure or wrap-around for at least one loop of the tubing 14. The bracket 36 may include two opposing cantilevered arms 38 extending outwardly from the base 28*a* in opposite direction such that the hollow tubing 14 may be wound around the anchored end of the two opposing cantilevered arms 38 and retained by the protruding portion so as to retain the hollow tubing 14 in a looping configuration. The bracket 36 may retain at least one loop of the hollow tubing 14 but may retain as many loops as is needed to circle the entire length of the hollow tubing 14. The bracket 36 may be oriented such that one arm extends toward the side of the housing 26 providing the opening 40 and the other arm extends in an opposite direction. In this respect, the hollow tubing 14 may be wound close to the point of attachment to the housing 26; however, the bracket 36 may be oriented in any direction with respect to the housing 26.

Figure 4:
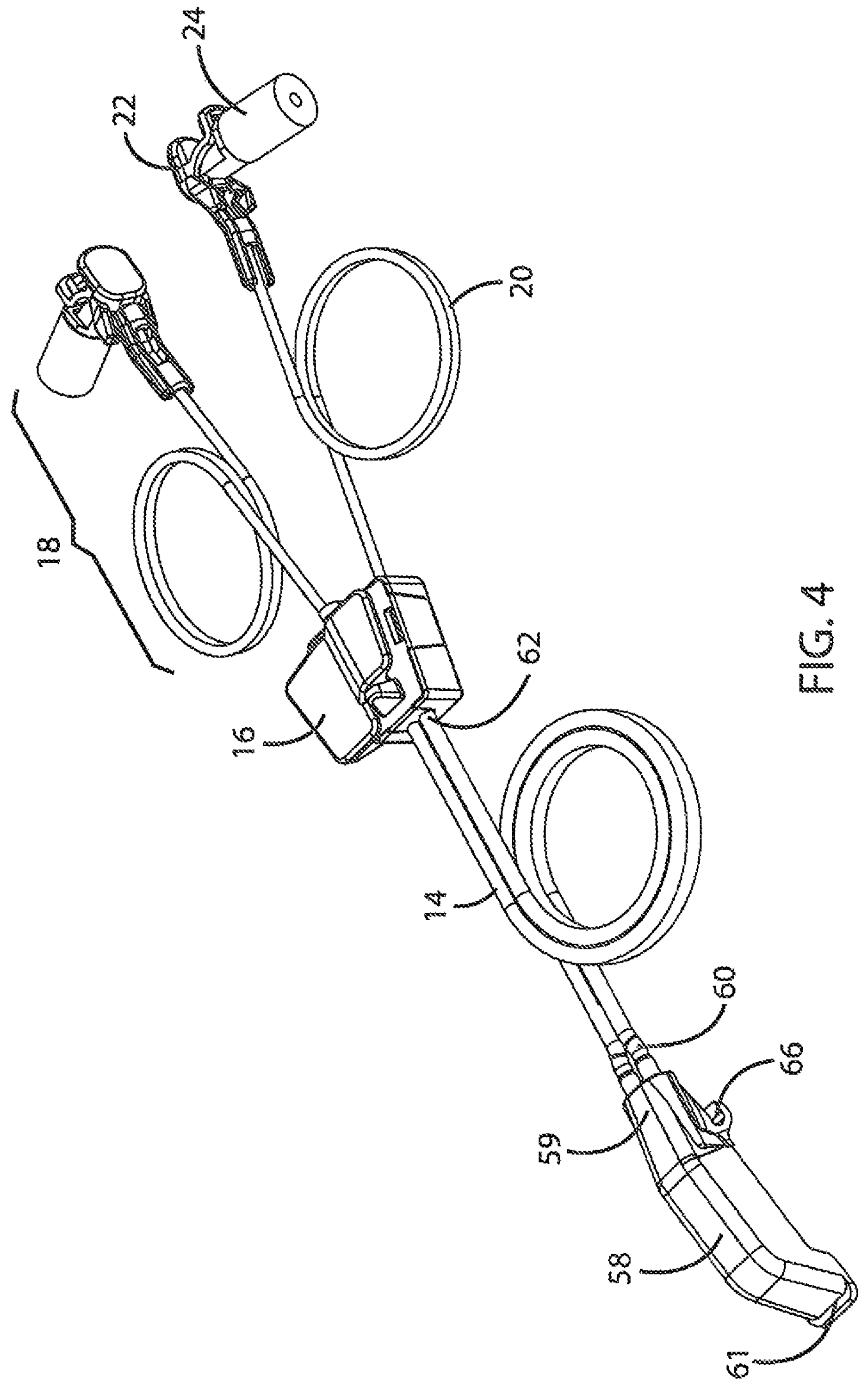
FIG. 4 is an isometric view of the pneumatic tubing attached to the headphones of FIG. 1 showing a quick disconnect coupler attached to the pneumatic tubing and a splitter connecting different segments of the pneumatic tubing together.
Figure 5:
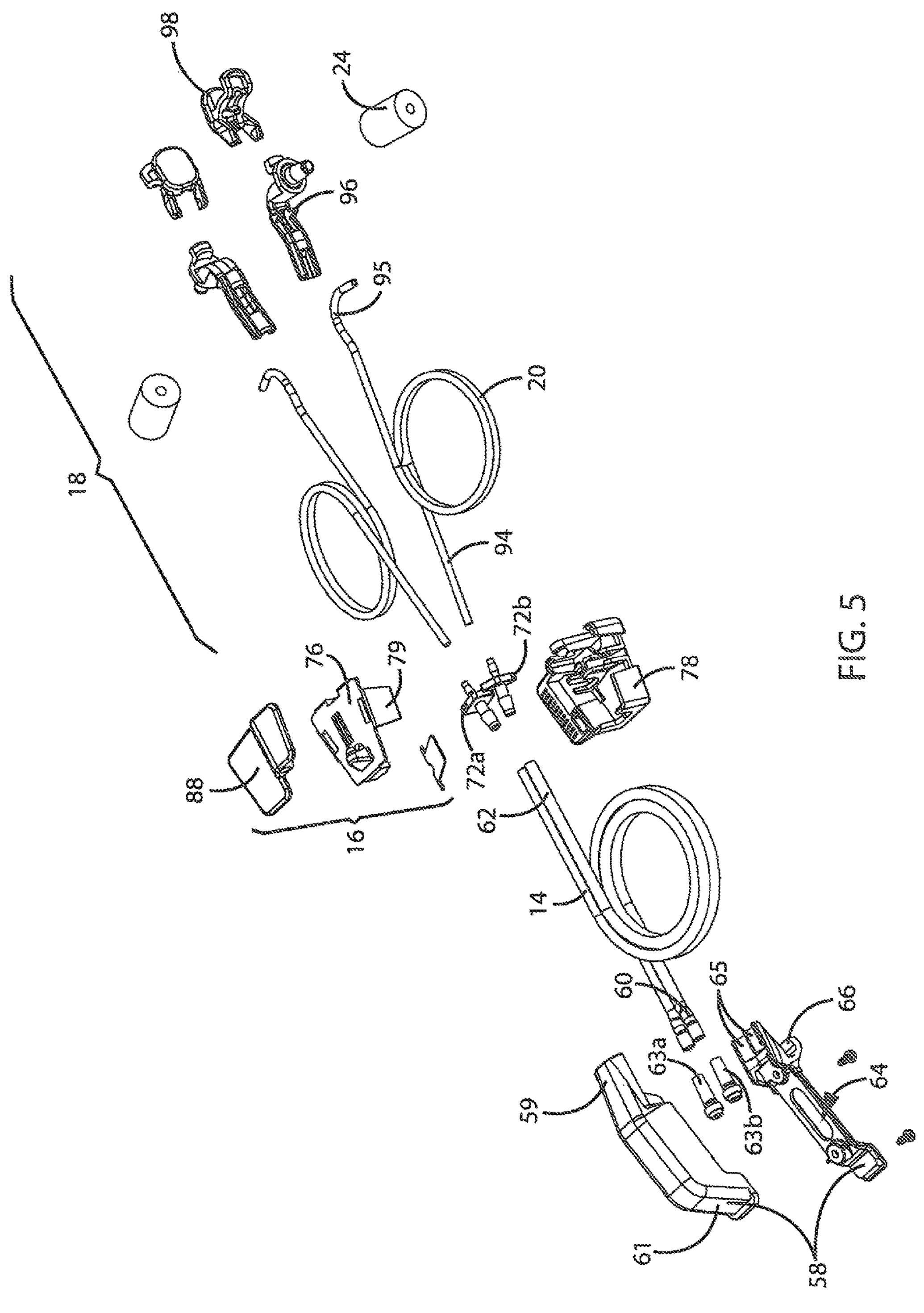
FIG. 5 is an exploded view of the pneumatic tubing and headphone assembly of FIG. 4.

Referring to FIGS. 4-5, the sound signals are communicated from the audio transducer 12 to the hollow tubing 14 and to the headphone assembly 18 terminating at the patient's ear canal. The hollow tubing 14 includes a first end 60, a second end 62, and extends a distance of between twenty-four and forty-eight inches and is preferably about thirty-six inches long, such that the audio transducer 12 may be held in a patient's hand or positioned along the side of a patient and the tubing 14 extends toward the patient's head. A first end 60 of the hollow tubing 14 is coupled to the housing 26 via the quick disconnect coupler 58 and a second end 62 of the hollow tubing is coupled to the headphone assembly 18 via the splitter 16. The first end 60 of the hollow tubing 14 may be attached to a pair of fittings 63*a*, 63*b* for attachment to the quick disconnect coupler 58. The fittings 63*a*, 63*b* may be hard plastic fittings providing a passage therethrough and have an outwardly extending rim to facilitate connection of the hollow tubing 14 to the quick disconnect coupler 58, as will be further discussed below.

Figure 6:
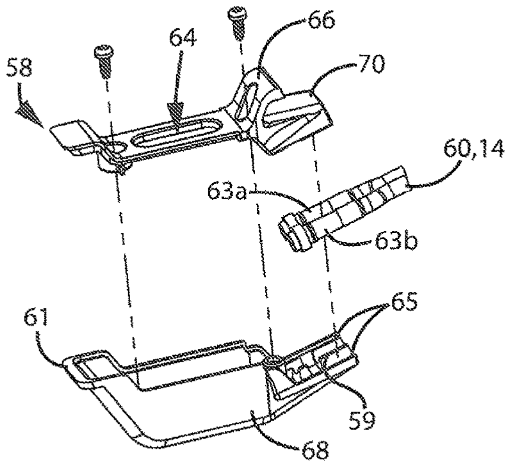
FIG. 6 is a partial exploded view showing the insertion of an end of the pneumatic tubing into the quick disconnect coupler.

Referring to FIG. 6, the quick disconnect coupler 58 provides a housing 68 for attachment to a housing backing 70. The quick disconnect coupler 58 provides a first end 59 opposite a second end 61 that are configured to grasp onto correspondingly located crevices of the housing 68 but may be easily released by pressing the release button 56 of the housing 26. The housing 68 provides two channels 65 therein at one end for receiving the fittings 63*a*, 63*b* within the channels 65. Each fitting 63*a*, 63*b* is inserted into a channel 65 of the hollow housing 68 such that the rims of the fittings 63*a*, 63*b* are supported within grooves of the channel 65 which retain the fittings 63*a*, 63*b* from outward movement in a direction along the passage of the fittings 63*a*, 63*b*. The open ends of the fittings 63*a*, 63*b* extend into the hollow enclosure of the housing 68.

The housing backing 70 may be attached to the housing 68 so as to enclose the hollow enclosure and to further restrain the fittings 63*a*, 63*b* within the quick disconnect coupler 58. The housing backing 70 may be attached to the housing 68 by screws. When the housing backing 70 is attached to the housing 68, the fittings 63*a*, 63*b* are secured within the quick disconnect coupler 58 and the housing 68 of the quick disconnect coupler 58 encloses the opening 40 in the audio transducer 12, defining a chamber through which sound is transmitted between the couplings 46*c*, 46*d* on the second end 45 of the two sided fitting 44 in the audio transducer 12 and the fittings 63*a*, 63*b* secured in the quick disconnect coupler 58.

The backing 70 may provide an outwardly extending hook 66 extending toward the first end 59 of the quick disconnect coupler 58 and configured to catch onto a crevice of the housing 26 of the audio transducer 12. An opening 64 is provided and generally centered within the housing backing 70. The opening 64 may be an oblong oval shape and sized to go over the two spaced passages 42*a*, 42*b* of the foam connector 41. It is contemplated that the opening 64 may be any shape, however, that goes over the spaced passages 42*a*, 42*b*. When the quick disconnect coupler 58 is attached to the housing 26, the two spaced passages 42*a*, 42*b* align with the opening 64 such that the sound signals coming through the two spaced passages 42*a*, 42*b* enter the opening 64 and travel into the chamber within the housing 68 of the quick disconnect coupler 58. The sound signals then continue through the fittings 63*a*, 63*b* and travel to the hollow tubing 14 as will be described further below.

Figure 7:
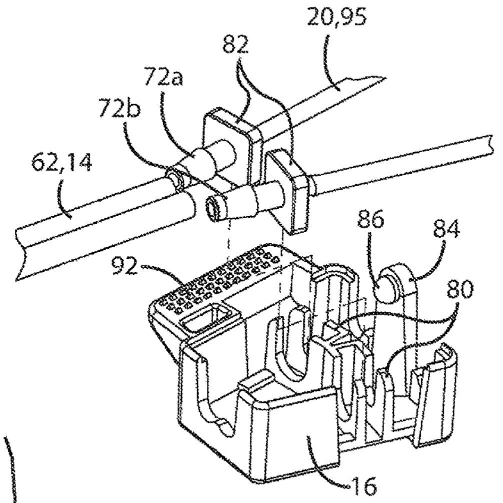
FIG. 7 is a partial exploded view showing the connection of the different segments of pneumatic tubing and insertion of the connector within the splitter.

Referring to FIG. 7, the second end 62 of the hollow tubing is connected to a pair of two sided fittings 72*a*, 72*b*. The two sided fittings 72*a*, 72*b* are conical or cylindrical stems or nozzles that provide an oppositely disposed nozzle on each end, each nozzle receiving tubing thereon for interconnection. The opposing nozzles may vary in size to connect tubing of different diameters. The stems of the two sided fittings 72*a*, 72*b* are connected to the hollow tubing 14 at one end and the MR invisible tubing 20 at the opposite end. The stems may be separated by a rectangular flange 82 which facilitates the installation of the two sided fittings 72*a*, 72*b* within the splitter 16 as further discussed below.

Figure 8:
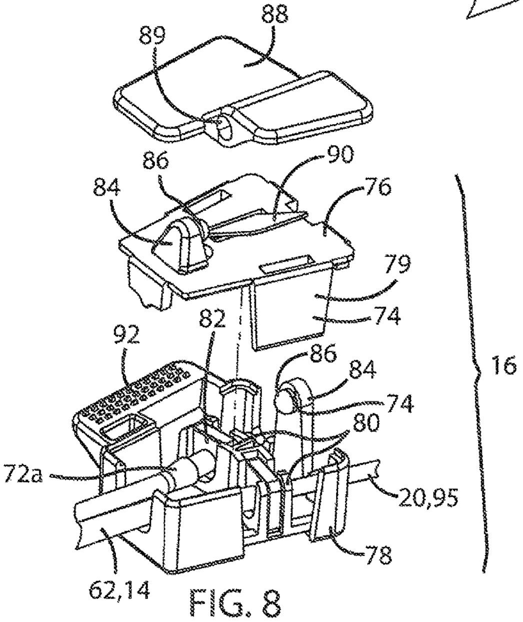
FIG. 8 is a partial exploded view showing assembly of the splitter housing to retain connection of the different segments of pneumatic tubing.

Referring to FIG. 8, the splitter 16 provides a splitter housing 74 having a top piece 76 and a bottom piece 78. The bottom piece 78 provides holders 80 for receiving the flanges 82 of the two sided fittings 72*a*, 72*b*. The holders 80 restrain the two sided fittings 72*a*, 72*b* in place and prevent movement. The top piece 76 is coupled to the bottom piece 78 to secure the two sided fittings 72*a*, 72*b* therein. The top piece 76 may include arms 79 surrounding the bottom piece 78 and snapping into place thereon.

The splitter housing 74 may provide two outwardly extending end pieces 84, one on the top piece 76 and one on the bottom piece 78, that are disposed apart and have inwardly facing bosses 86 for receiving a clip piece 88 therebetween. The clip piece 88 may provide opposing openings 89 allowing the bosses 86 to be inserted within the openings 89 and to snap the clip piece 88 into place between the bosses 86. A spring 90 may bias the clip piece 88 toward the bottom piece 78. The bottom piece 78 may include a grooved mating portion 92 to provide a clip when the clip piece 88 and bottom piece 78 come together.

Figure 9:
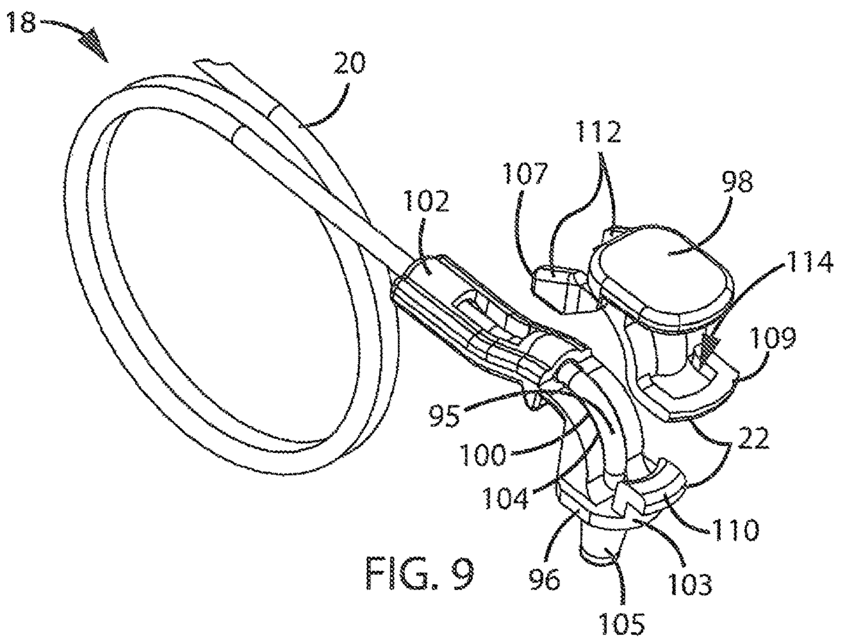
FIG. 9 is an isometric view of an ear bud of the headphone assembly showing the pneumatic tubing installed within the bottom housing of the tubing retainer and the top housing of the tubing retainer uninstalled.

Referring also to FIG. 9, the headphone assembly 18 is connected to the splitter 16 via the MR invisible tubing 20 attached to the opposite end of the two sided fitting reducers 72*a*, 72*b*. The MR invisible tubing 20 includes a first end 94 and a second end 95 extending a distance of between eight and twenty-four inches and is preferably about sixteen inches in length. A first end 94 of the MR invisible tubing 20 is coupled to the splitter 16 and a second end 95 of the MR invisible tubing terminates at the tubing retainer 22 which is positioned within the patient's ear.

A tubing retainer 22 provides a fixed structure for routing the MR invisible tubing 20 to the patient's ear. The retainer 22 includes a lower housing 96 receiving the MR invisible tubing 20 and an upper housing 98 coupled to the lower housing 96 to retain the MR invisible tubing 20 in place and prevent further movement of the MR invisible tubing 20 with respect to the retainer 22.

With reference also to FIGS. 11-16, the lower housing 96 provides a channel 100 extending from a first end 102 of the lower housing 96 to an opposite second end 103 of the lower housing 96. The lower housing 96 also includes at least one arched surface 111 extending over the channel 100 and configured to retain tubing within the channel 100. The channel also includes a bent portion 104. The bent portion 104 is defined by an arcuate surface 101 extending longitudinally along lower housing with the channel 100. The arcuate surface 101 and the channel 100 provide a guide along which the MR invisible tubing 20 is bent without causing the MR invisible tubing 20 to become kinked or occluded. The bent portion 104 allows the MR invisible tubing 20 to transition from extending along the patient's body to be inserted into the ear canal. The bend may have an angle of approximately ninety degrees or, in other words, be at a perpendicular angle. The arcuate surface 101 ensures that the MR invisible tubing 20 is not bent around a sharp angular corner that would reduce partially or wholly occlude the tubing and thereby reduce sound transmission efficiency. The channel 100 terminates at a horn or funnel-shaped nozzle guide 105 mounted at the end of the lower housing 96.

The MR invisible tubing 20 is routed in the channel 100 and under a first arched surface 111 at the first end 102 of the lower housing 96 whereby the channel 100 may be enclosed to encircle the MR invisible tubing 20. The MR invisible tubing 20 then continues to extend along the channel 100 and under a second arched surface 111 proximate the bent portion 104. The channel supports the bottom half of the MR invisible tubing 20 and the second arched surface 111 retains the MR invisible tubing 20 within the channel as it is then routed within the channel 100 over the bent portion 104 of the lower housing 96. The MR invisible tubing 20 is then inserted within the nozzle guide 105. The MR invisible tubing 20 may extend into the nozzle guide 105 and terminate within or may extend slightly out of the nozzle guide 105. However, the nozzle guide 105 may also take a cylindrical or other tubular shape.

As discussed above, the MR invisible tubing 20 is slidably inserted into the channel 100 of the lower housing 96. The length of the tubing 20 inserted and the length of the tubing 20 extending beyond the end of the nozzle guide 105 is adjusted by sliding the MR invisible tubing 20 along the channel. In order to retain the MR invisible tubing 20 longitudinally within the retainer 22, the upper housing 98 is snapped onto the lower housing 96. With reference also to FIGS. 17-22, the upper housing 98 includes a first end 107 and a second end 109, opposite the first end 107. The first end 107 of the upper housing 98 may include two arms 112 extending downward, and each arm 112 includes a tab 113 that projects inward from the arm 112 toward a center axis of the upper housing 98. As the upper housing 98 is pressed downward over the lower housing 96, the width between the tabs 113 is less than the width of the lower housing 96 such that the arms 112 are initially biased apart from each other. As the upper housing 98 is pressed further onto the lower housing 96, the arms 112 are long enough such that the tabs 113 extend below the body of the lower housing 96 and snap back toward each other around the lower housing 96. A second end 109 of the upper housing 98 includes an arcuate retaining member 115 protruding outward from and extending between each side of the upper housing 98. The arcuate retaining member 115 defines a slot 114 behind the arcuate retaining member 115 configured to engage an outwardly extending tab 110 on the lower housing 96. In this respect, the upper housing 98 and lower housing 96 may be joined by placing second end 109 and the arcuate retaining member 115 of the upper housing 98 down over the tab 110 on the lower housing 96. The first end 107 of the upper housing 98 may then be pivoted downwards about the tab 110, pressing the arms 112 over the body of the lower housing 96. The upper housing 98 is further pivoted until the arms 112 extend below the body of the lower housing 96 and the tabs 113 snap around the lower housing 96.

The upper housing 98 also serves to prevent further longitudinal movement of the MR invisible tubing 20 within the lower housing 96. The upper housing 98 has a rear body 120 that extends in a plane generally tangential to and displaced from the bent portion 104 of the lower housing 96. A channel 122 is formed on the interior surface of the rear body 120. The channel 122 on the rear body 120 of the upper housing 96 is generally aligned with and opposite from the channel 100 in the lower housing 96 when the two housings 96, 98 are joined together. The diameter of the complete passage formed by the channel 100 in the lower housing 96 and the channel 122 in the upper housing 98 is slightly less than the diameter of the tubing 20 fit through the passage. The difference in diameter is sufficient to grip the tubing 20 and restrict movement along the passage but not sufficient to cause occlusion of the tubing 20 and thereby reduce or prevent the quality of the sound traveling through the tubing 20.

Figure 10:
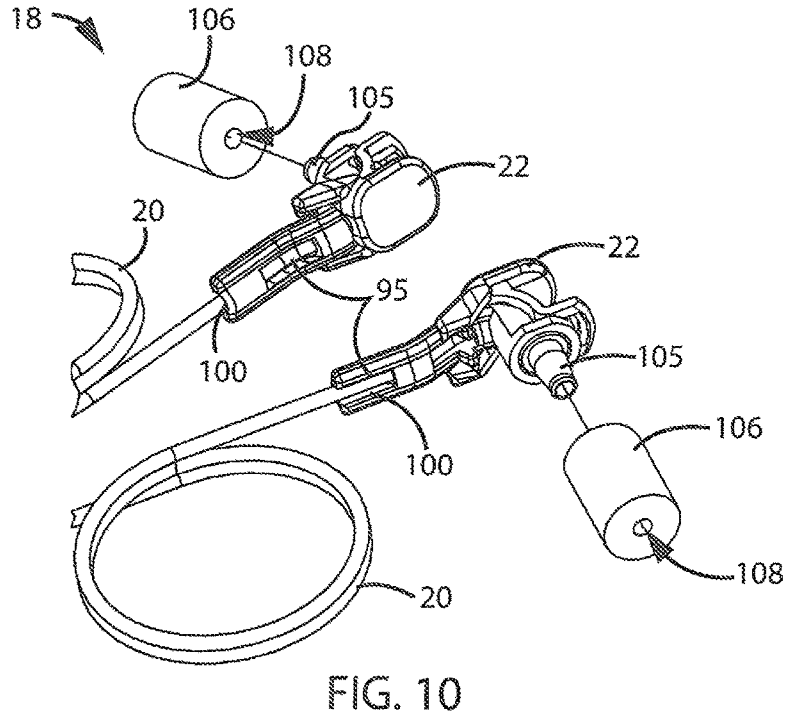
FIG. 10 is an isometric view of the ear buds of the headphone assembly with the top housing of the tubing retainer installed to the bottom housing of the tubing retainer and showing how the ear plugs are installed on a nozzle guide of the tubing retainer.
Figure 11:
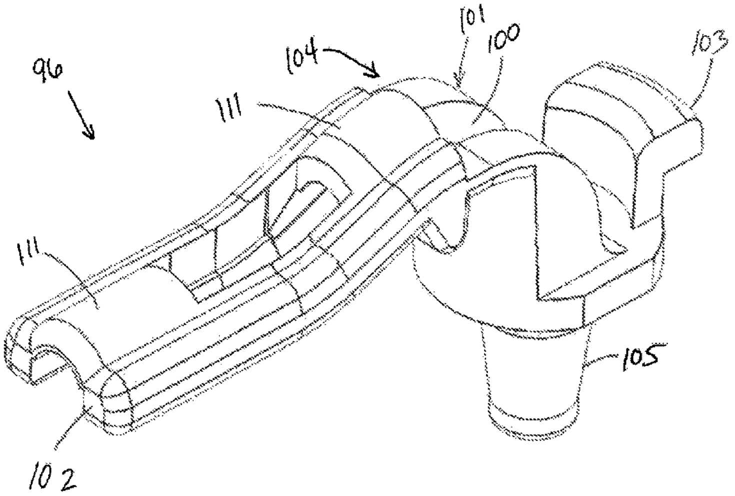
FIG. 11 is an isometric view of a lower housing for a tubing retainer used with the headphone assembly of FIG. 1.
Figure 12:
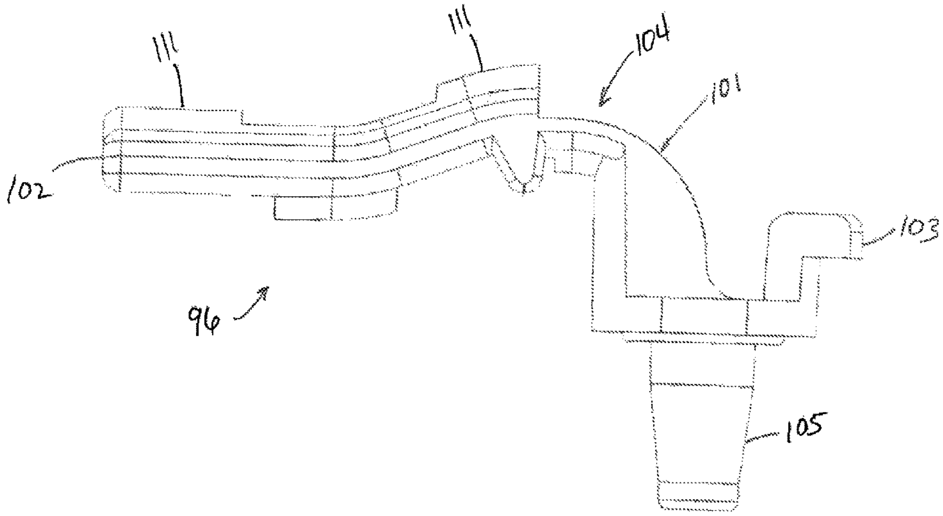
FIG. 12 is a side elevation view of the lower housing for the tubing retainer used with the headphone assembly of FIG. 1.
Figure 13:
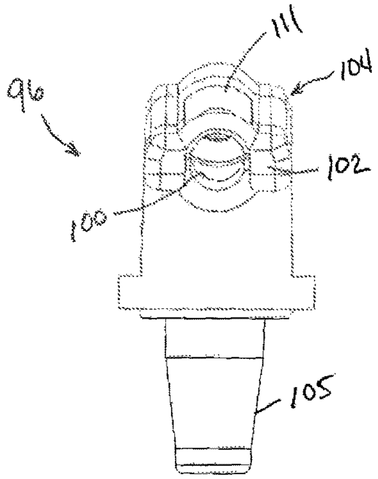
FIG. 13 is a bottom plan view of the lower housing for the tubing retainer used with the headphone assembly of FIG. 1.
Figure 14:
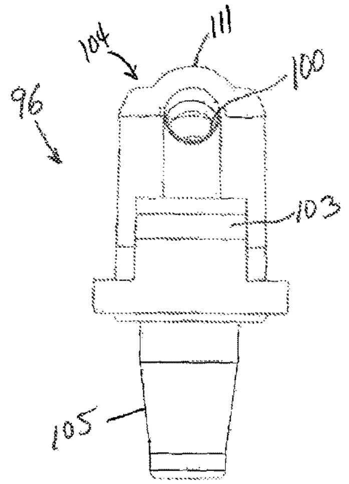
FIG. 14 is a top plan view of the lower housing for the tubing retainer used with the headphone assembly of FIG. 1.
Figure 15:
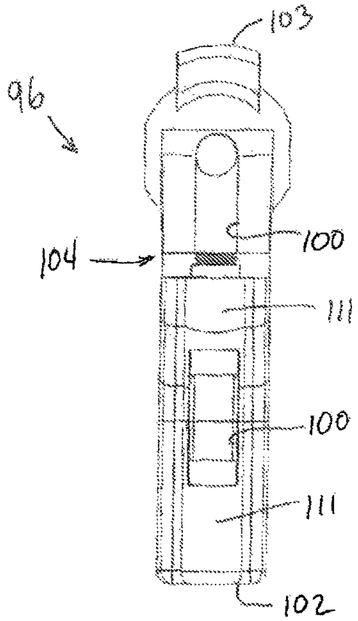
FIG. 15 is a rear elevation view of the lower housing for the tubing retainer used with the headphone assembly of FIG. 1.
Figure 16:
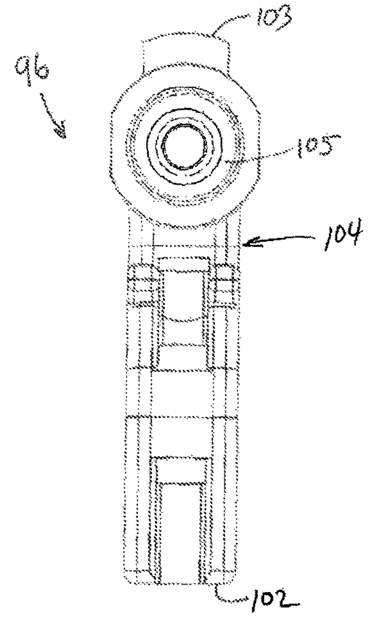
FIG. 16 is a front elevation view of the lower housing for the tubing retainer used with the headphone assembly of FIG. 1.
Figure 17:
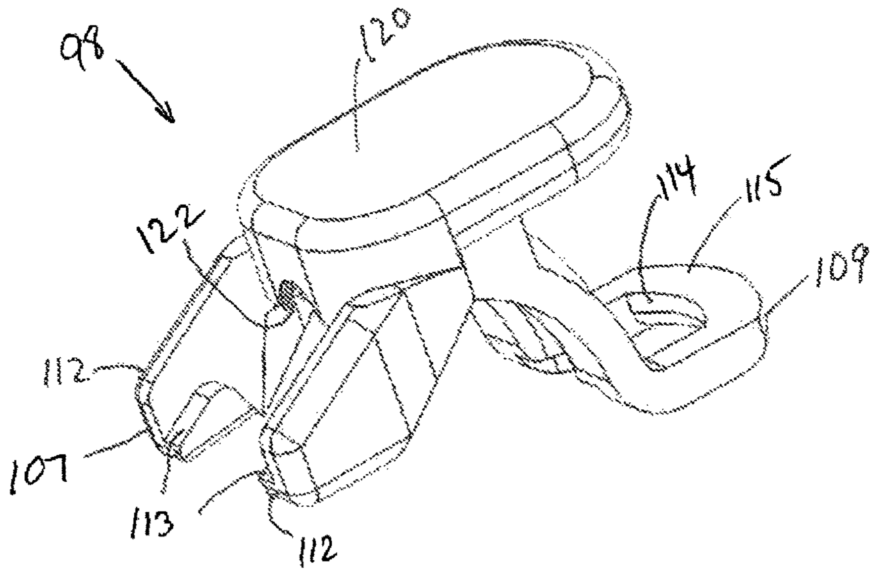
FIG. 17 is an isometric view of an upper housing for the tubing retainer used with the headphone assembly of FIG. 1.
Figure 18:
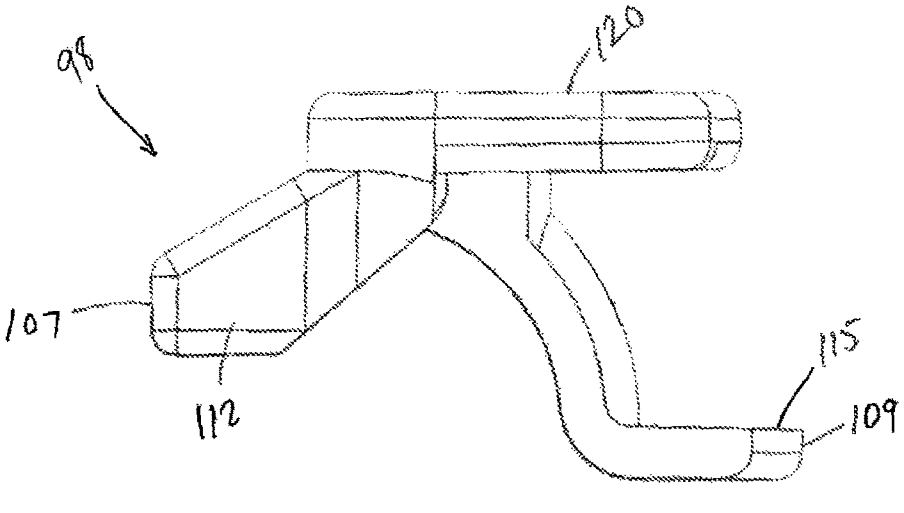
FIG. 18 is a side elevation view of the upper housing for the tubing retainer used with the headphone assembly of FIG. 1.
Figure 19:
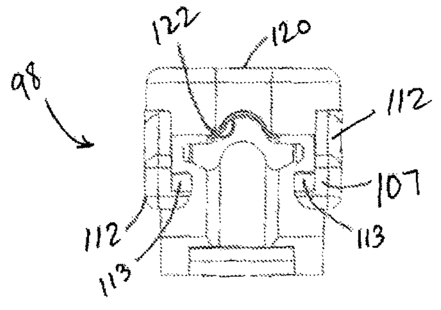
FIG. 19 is a bottom plan view of the upper housing for the tubing retainer used with the headphone assembly of FIG. 1.
Figure 20:
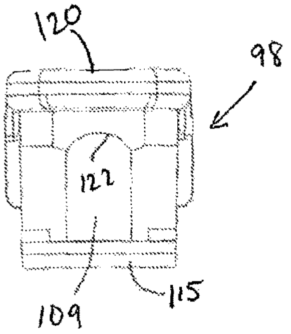
FIG. 20 is a top plan view of the upper housing for the tubing retainer used with the headphone assembly of FIG. 1.
Figure 21:
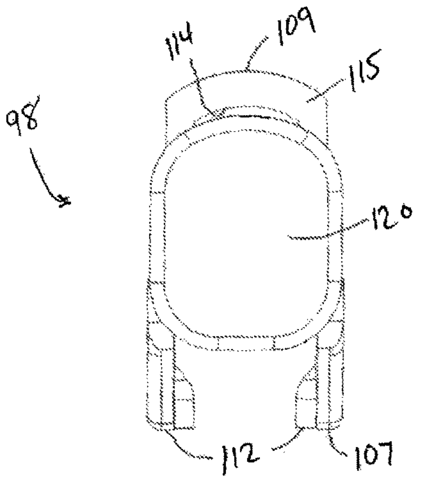
FIG. 21 is a rear elevation view of the upper housing for the tubing retainer used with the headphone assembly of FIG. 1.
Figure 22:
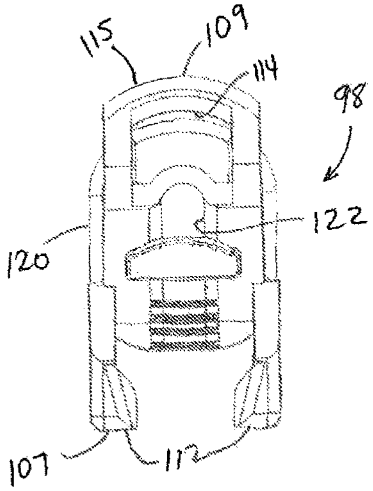
FIG. 22 is a front elevation view of the upper housing for the tubing retainer used with the headphone assembly of FIG. 1.

Referring to FIG. 10, once the retainer 22 is assembled, an ear canal plug 106 may be inserted over the nozzle guide 105 of the retainer 22. The ear canal plug 106 may be a cylindrical foam, rubber or spongy material having a passageway 108 extending between first and second ends of the plug 106. The plug 106 may be inserted onto the nozzle guide 105 by placing the nozzle guide 105 partly within the passageway 108. The ear canal plug 106 may be different lengths and/or diameters depending on the size of the patient's ear canal, and may be positioned within the patient's ear canal to isolate the ear canal from external noises. The MR invisible tubing 20 extends through the passageway 108 in the plug 106 to prevent occlusion of the passageway when the ear plug 106 is inserted into the patient's ear and to provide a passage for the sound signals to travel into the patient's ear. In addition to allowing the desired communication to pass into the patient's ear, the ear plug 106 fills the ear canal to reduce the level of ambient sound generated, for example, by an MR scanner to pass into the patient's ear.

In an alternative embodiment, the headphone assembly 18 may also include a microphone for allowing the patient to speak into the microphone and transmit sound back to the audio transducer 12. The audio transducer 12 may then wirelessly transmit the sound signals to another person such as a family member or a health care professional in an adjacent control room. Optionally, the audio transducer 12 may be connected to a wireless network and transmit the sound signals to another person within the noisy environment who is wearing a similar headphone assembly, allowing communication between people while also providing hearing protection in a noisy environment. The headphone assembly 18 may also include audio controls, such as volume control buttons which allow the patient to adjust the sound volume.

In operation, the pneumatic audio system 10 may be assembled by attaching the quick disconnect coupler 58 to the cylindrical housing 26 of the audio transducer 12. The opposite ends 59, 61 of the quick disconnect coupler 58 are snapped into the crevices of the housing 26. When it is desired for the cylindrical housing 26 to be separated from the audio transducer 12, the release button 56 is pressed allowing one end 59 of the quick disconnect coupler 58 to be removed from the housing 26. The ear canal plugs 106 may be placed within the ear canal of the patient. The ear canal plugs 106 serve to isolate the inner ear from ambient noise by blocking ambient sounds from entering the ear canal. The ear plugs 106 also allow communication with the patient via the tubing 20 passing through the passageway 108 within the ear plug 106. The clip piece 88 of the splitter 16 may be attached to the patient's clothing to prevent accidental removal of the headphone assembly 18 from the patient's ears.

Using an audio transmitter (not shown) located, for example, in a scan room, a family member, the healthcare professional, or another person may communicate through a microphone coupled to the audio transmitter. The audio signals are then wirelessly transmitted to the audio receiver of the audio transducer 12. Received by the audio receiver, and converted into audio signals, the signals are received by the speakers 48*a*, 48*b*. The speakers 48*a*, 48*b* translate the signals to audible sound. The audible sound then travels through the Y-connector 57, through the two sided fitting 44, through the quick disconnect coupler 58, through the clear tubing 14, through the fittings 72*a*, 72*b*, and through the MR invisible tubing 20 into the patient's ear canal.

It is noted that the pneumatic audio system 10 may also allow communication between a health care professional and the patient without the use of the audio transducer 12. If, for example, during preparation for an imaging scan and/or between successive imaging scans, the health care professional needs to communicate with the patient and the ear plugs 106 have already been inserted into the patient's ears, the health care professional may disconnect the quick disconnect coupler 58 and speak directly into the opening 64 of the quick disconnect coupler 58. The sound is then transmitted along the tubing 14, 20 in the same manner as if it were transmitted the audio transducer 12. When the health care professional is done communicating to the patient, the quick disconnect coupler 58 is reconnected to the housing 26 of the audio transducer 12 and the health care professional may again communicate via a microphone and an audio transmitter as discussed above.

When the headphone assembly 18 is used in conjunction with MR imaging, the MR scanner alternately generates a strong magnetic field and then detects the faint nuclear magnetic resonance (NMR) signals given off by nuclei of materials that are in the presence of the magnetic field. One element that generated NMR signals in response to the magnetic field is hydrogen. Because the body and components of the body include in varying degrees water, which includes two hydrogen atoms and one oxygen atom, the various tissues of the body are well suited to generating NMR signals in response to the magnetic field. The strength of the NMR signals generated within the body vary as a function of the type of organ, bone, tissue, etc. . . . present within the magnetic field. Similarly, other materials which are present within the bore of the scanner may also generate NMR signals which may be detected by imaging coils and which will show up on the images generated by the MR scanner. Objects that show up in MR images that are undesirable may be referred to as proton signal artifacts.

The MR invisible tubing 20 may be used, for example, when imaging the head of a patient, and does not generate any proton signal artifacts in the resultant MR image. The MR invisible tubing 20 is preferably a plastic tubing having sufficient flexibility to allow the tubing to be positioned around the patient, yet sufficient durability to avoid being cracked, punctured, or otherwise damaged during standard MR procedures. As indicated above, hydrogen reacts to the magnetic field generated by the MR scanner and generated NMR signals. Because hydrogen is one of the elemental components of plastic, plastic tubing commonly generates proton signal artifacts when used during MR imaging. Thus, the MR invisible tubing 20 is a plastic material in which at least a portion of, or preferably all of, the hydrogen has been replaced by another element or elements that do not generate NMR signals in the presence of the magnetic field. As a result, the magnitude of the proton signal artifact is reduced or eliminated. According to one embodiment of the invention, hydrogen is replaced by a halogen in the plastic.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A sound system for use in a magnetic field environment, comprising:
- an audio transducer including
  - a housing having a plurality of walls,
  - a sound insulating insert supported within the housing, and
  - a speaker supported by the sound insulating insert and extending at an angle with respect to the walls of the housing, wherein the speaker is spaced apart from each of the plurality of walls of the housing by the sound insulating insert;
- a hollow tube coupled to the audio transducer at a first end and configured to transmit audio signals from the speaker through the tube, wherein the hollow tube is a plastic material that replaces hydrogen with an element that does not generate a proton signal artifact responsive to a magnetic field generated by an MR scanner;
- a headphone coupled to a second end of the hollow tube and configured to deliver audio signals to an ear canal of a human user.

2. The sound system of claim 1 wherein the housing includes a port receiving an end of the hollow tube and releasably mounted to the housing.

3. The sound system of claim 1 wherein the housing includes an outwardly extending bracket permitting the hollow tube to be wrapped around the bracket for storage.

4. The sound system of claim 1 wherein the speaker is a piezoelectric speaker.

5. The sound system of claim 1 wherein the hollow tube includes:
- a first hollow tube;
- a second hollow tube, wherein the second hollow tube is not excited by the magnetic field environment, such that it is not visible on an MR image; and
- a fitting connecting the first hollow tube to the second hollow tube.

6. A sound system for use in a magnetic field environment, comprising:
- an audio transducer including:
  - a housing having a plurality of walls,
  - a sound insulating insert supported within the housing, and
  - a speaker supported by the sound insulating insert and extending at an angle with respect to the walls of the housing, wherein the speaker is spaced apart from each of the plurality of walls of the housing by the sound insulating insert;
- a first hollow tube coupled to the audio transducer and configured to transmit audio signals from the speaker through the tube;
- a second hollow tube, wherein the second hollow tube is a plastic material that replaces hydrogen with an element that does not generate a proton signal artifact responsive to the magnetic field generated by an MR scanner;
- a fitting connecting the first hollow tube to the second hollow tube; and
- a headphone coupled to the second hollow tube and configured to deliver audio signals to an ear canal of a human user.

7. The sound system of claim 1 wherein the audio transducer further includes:
- an RF receiver operable to wirelessly receive an audio signal, and
- a processor operable in communication with the RF receiver and the speaker, wherein the processor transmits the audio signal to the speaker.

8. A pneumatic audio system for use during magnetic resonance (MR) imaging, comprising:
- an audio transducer;
- a first hollow tube having a first end and a second end wherein the audio transducer is connected at the first end of the first hollow tube;
- a second hollow tube having a first end and a second end wherein the first end of the second hollow tube is connectable to the second end of the first hollow tube;
- an earphone wherein the second end of the second hollow tube is connectable to the earphone;
- wherein the second hollow tube is a plastic material that replaces hydrogen with an element that does not generate a proton signal artifact responsive to the magnetic field generated by an MR scanner, such that it is not visible on an MR image.

9. The system of claim 8 further including a fitting coupling the first hollow tube to the second hollow tube.

10. The system of claim 9 further comprising a housing receiving the fitting.

11. The system of claim 10 wherein the housing has a clip for attachment to a patient.

12. An earphone for transmitting and receiving audio signals, comprising:
- a hollow tubing configured to transmit audio signals therethrough;
- a retainer including:
  - a first housing member providing a channel for receiving the hollow tubing,
  - a bent portion to change the direction of the hollow tubing,
  - an arcuate surface extending along the bent portion and along which the channel extends to guide the hollow tubing around the bend portion, and
  - a nozzle guide having an opening extending therethrough to receive the hollow tubing; and
- a plug for insertion into an ear canal having a passageway sized therein for receiving the hollow tubing, wherein the hollow tubing is received in the channel, extends through the nozzle guide, and terminates proximate the end the of the plug inserted into the ear canal.

13. The earphone of claim 12 wherein the retainer further includes a second housing member removably coupled to the first housing member and preventing translation of the hollowing tubing along the channel.

14. The earphone of claim 12 wherein the ear canal plug is a foam plug.

15. The earphone of claim 14 wherein the nozzle guide extends partly within the passageway of the plug.

16. The earphone of claim 15 wherein the nozzle guide has a length less than a length of the plug.

17. The earphone of claim 12 wherein the hollow tubing is a plastic material that does not generate a proton signal artifact responsive to the magnetic field generated by an MR scanner.

* * * * *